(12) United States Patent
Crawford et al.

(10) Patent No.: US 11,771,444 B2
(45) Date of Patent: Oct. 3, 2023

(54) MEDICAL INSTRUMENT HAVING A BALLOON AND AN EXTRACTION MEMBER

(71) Applicant: Boston Scientific Scimed, Inc., Maple Grove, MN (US)

(72) Inventors: Richard Crawford, Athenry (IE); Martin Lawrence Fawdry, Galway (IE); Louis McNern, Killybegs (IE); Aiden Flanagan, Kilcolgan (IE); Matthew Montague, Oranmore (IE); Geraldine Alice Toner, Lifford (IE); Enda Connaughton, Craughwell (IE); Gary Gilmartin, Foxford (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 228 days.

(21) Appl. No.: 17/223,805

(22) Filed: Apr. 6, 2021

(65) Prior Publication Data

US 2021/0315595 A1    Oct. 14, 2021

Related U.S. Application Data

(60) Provisional application No. 63/006,793, filed on Apr. 8, 2020.

(51) Int. Cl.
*A61B 17/22*    (2006.01)
(52) U.S. Cl.
CPC .... *A61B 17/22* (2013.01); *A61B 2017/22038* (2013.01); *A61B 2017/22051* (2013.01); *A61B 2017/22084* (2013.01)

(58) Field of Classification Search
CPC . A61B 17/22; A61B 17/22032; A61B 17/221; A61B 2017/22038;
(Continued)

(56) References Cited

U.S. PATENT DOCUMENTS 4,295,464 A    10/1981  Shihata
4,467,806 A     8/1984  Bhiwandiwala et al.
(Continued)

FOREIGN PATENT DOCUMENTS

AU    683471 B2    2/1995
AU    736519 B2    9/2000
(Continued)

OTHER PUBLICATIONS

Partial International Search Report and Provisional Opinion issued in International Application No. PCT/US2021/025999 dated Jun. 25, 2021 (15 pages).

*Primary Examiner* — Jocelin C Tanner
(74) *Attorney, Agent, or Firm* — Bookoff McAndrews PLLC

(57) ABSTRACT

A medical instrument may include a tube, a sheath provided around and coaxial with the tube, and an inflatable balloon at a distal end of the sheath. The balloon may receive a fluid from a lumen of the sheath, and may have a central opening along a longitudinal axis thereof, and into which the tube extends, a proximal portion, a middle portion adjacent to and distal of the proximal portion, and a distal portion adjacent to and proximal of the middle portion. When the balloon is inflated with the fluid, a maximum diameter of the middle portion may be less than a maximum diameter of the proximal portion, and less than a maximum diameter of the distal portion. The medical instrument may also include an extraction member provided at a distal end of the tube, distal to the balloon, and movable axially relative to the balloon.

20 Claims, 8 Drawing Sheets

(58) Field of Classification Search
CPC ........... A61B 2017/22051; A61B 2017/22069;
A61B 2017/22084; A61M 25/0026;
A61M 25/0662; A61M 25/1002; A61M
25/1011; A61M 29/02; A61M 2025/0681;
A61M 2025/0687; A61M 2025/1015;
A61M 2025/1079; A61M 2025/109;
A61M 2210/1075
See application file for complete search history.

(56) References Cited

U.S. PATENT DOCUMENTS

| | | | |
|---|---|---|---|
| 4,781,677 A | 11/1988 | Wilcox | |
| 4,784,133 A * | 11/1988 | Mackin | A61B 1/3137 606/7 |
| 4,911,163 A | 3/1990 | Fina | |
| 5,324,260 A * | 6/1994 | O'Neill | A61M 25/10182 604/103.08 |
| 5,514,073 A * | 5/1996 | Miyata | A61M 60/531 600/18 |
| 5,772,674 A * | 6/1998 | Nakhjavan | A61B 17/22032 606/159 |
| 6,488,653 B1 * | 12/2002 | Lombardo | A61M 25/1002 604/103.06 |
| 6,692,484 B1 | 2/2004 | Karpiel et al. | |
| 8,403,976 B2 | 3/2013 | Sachar et al. | |
| 8,740,842 B2 * | 6/2014 | Weber | A61M 25/10 604/96.01 |
| 2005/0059965 A1 * | 3/2005 | Eberl | A61M 25/10 606/41 |
| 2005/0197530 A1 * | 9/2005 | Wallace | A61B 5/0084 600/116 |
| 2010/0022970 A1 * | 1/2010 | Hirszowicz | A61B 17/22032 604/268 |
| 2011/0275990 A1 * | 11/2011 | Besser | A61B 18/245 604/99.01 |
| 2012/0259215 A1 * | 10/2012 | Gerrans | A61M 25/1011 604/509 |
| 2015/0150572 A1 | 6/2015 | Kumbhari et al. | |
| 2015/0314111 A1 * | 11/2015 | Solar | A61M 25/1011 604/509 |
| 2016/0242799 A1 | 8/2016 | Bonneau et al. | |
| 2016/0287371 A1 | 10/2016 | Smith et al. | |
| 2016/0338707 A1 | 11/2016 | Vogel et al. | |

FOREIGN PATENT DOCUMENTS

| | | |
|---|---|---|
| DE | 3438131 C2 | 4/1986 |
| EP | 0200668 A2 | 11/1986 |
| EP | 1593375 A1 | 11/2005 |
| EP | 2002779 A2 | 12/2008 |
| WO | 84/01513 A1 | 4/1984 |
| WO | 2005/041788 A1 | 5/2005 |
| WO | 2007/004221 A1 | 1/2007 |
| WO | 2008/004238 A2 | 1/2008 |

* cited by examiner

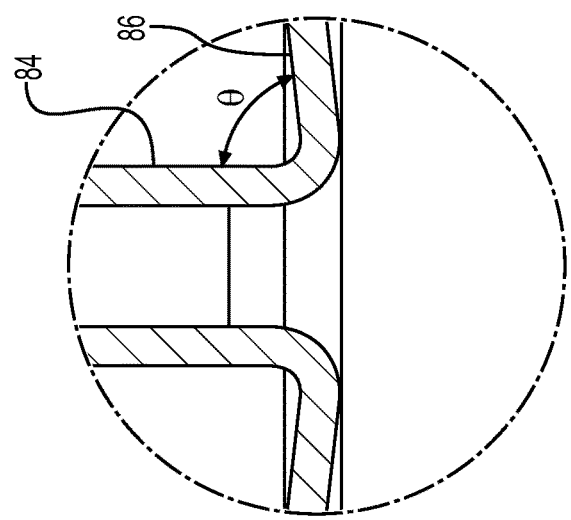
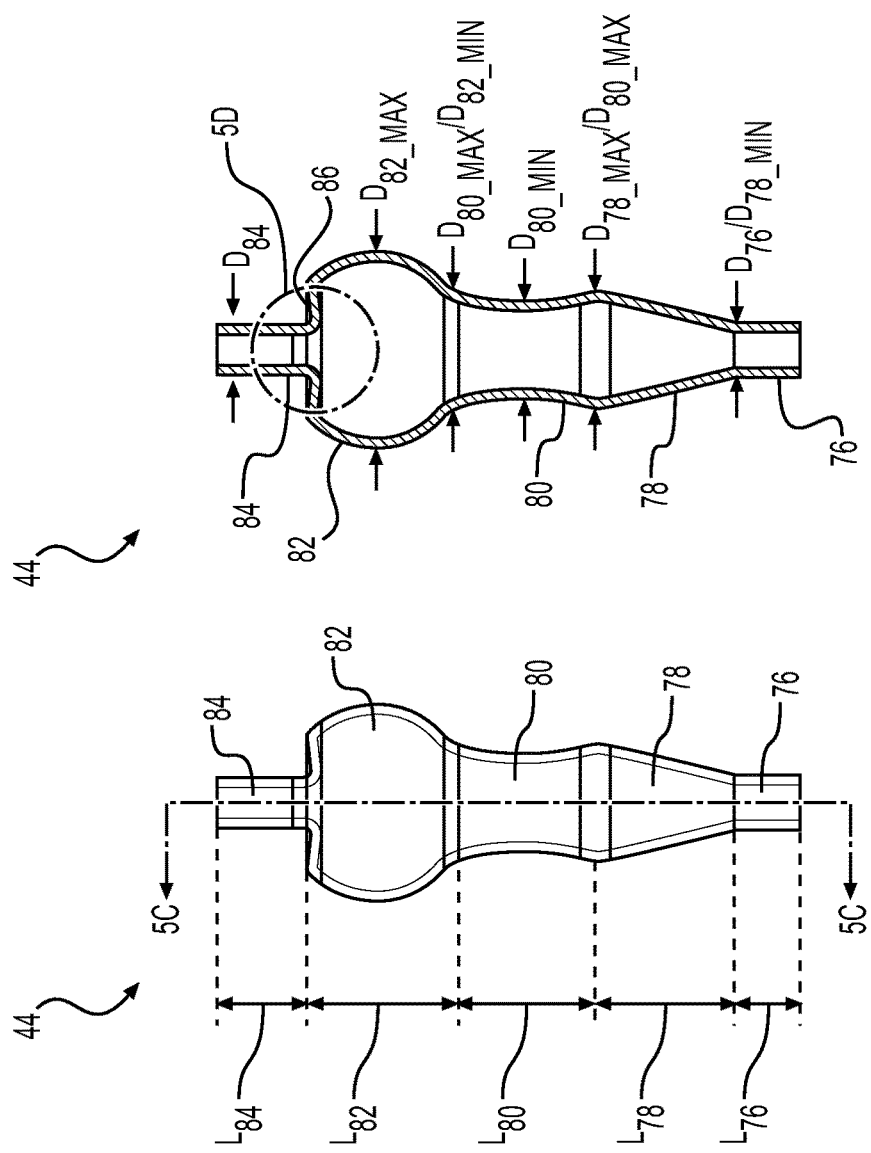
FIG. 5D
FIG. 5C
FIG. 5B

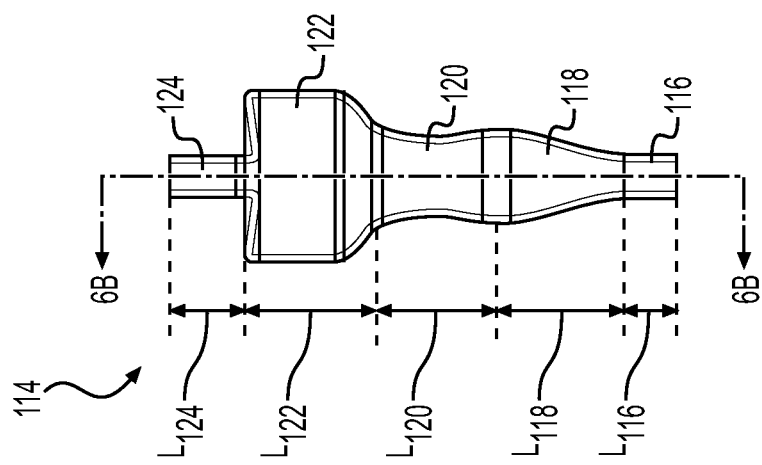
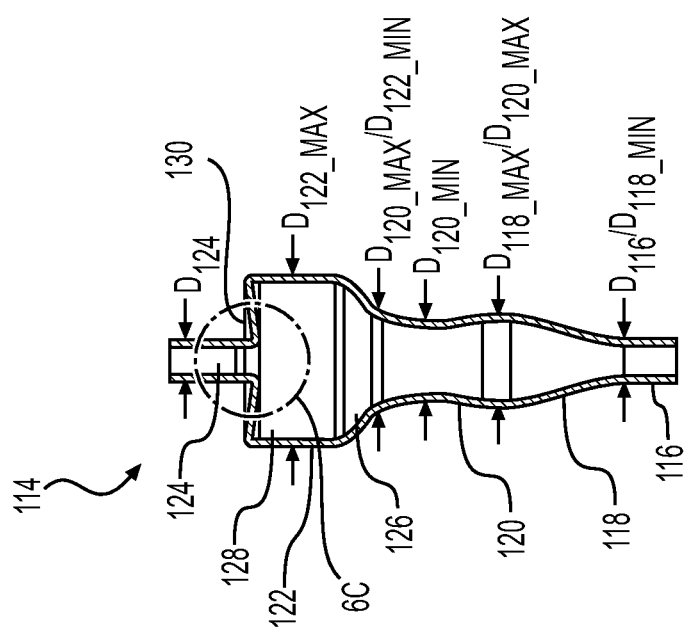
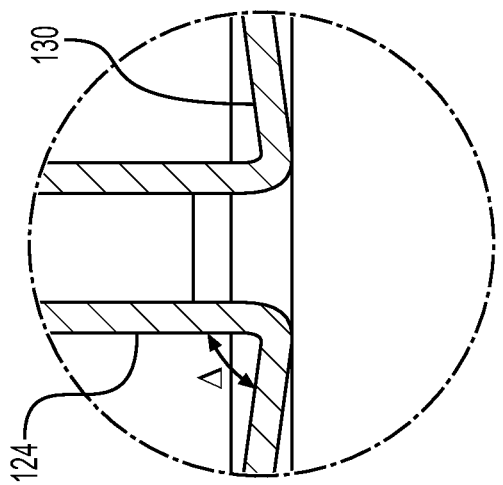
FIG. 6A
FIG. 6B
FIG. 6C

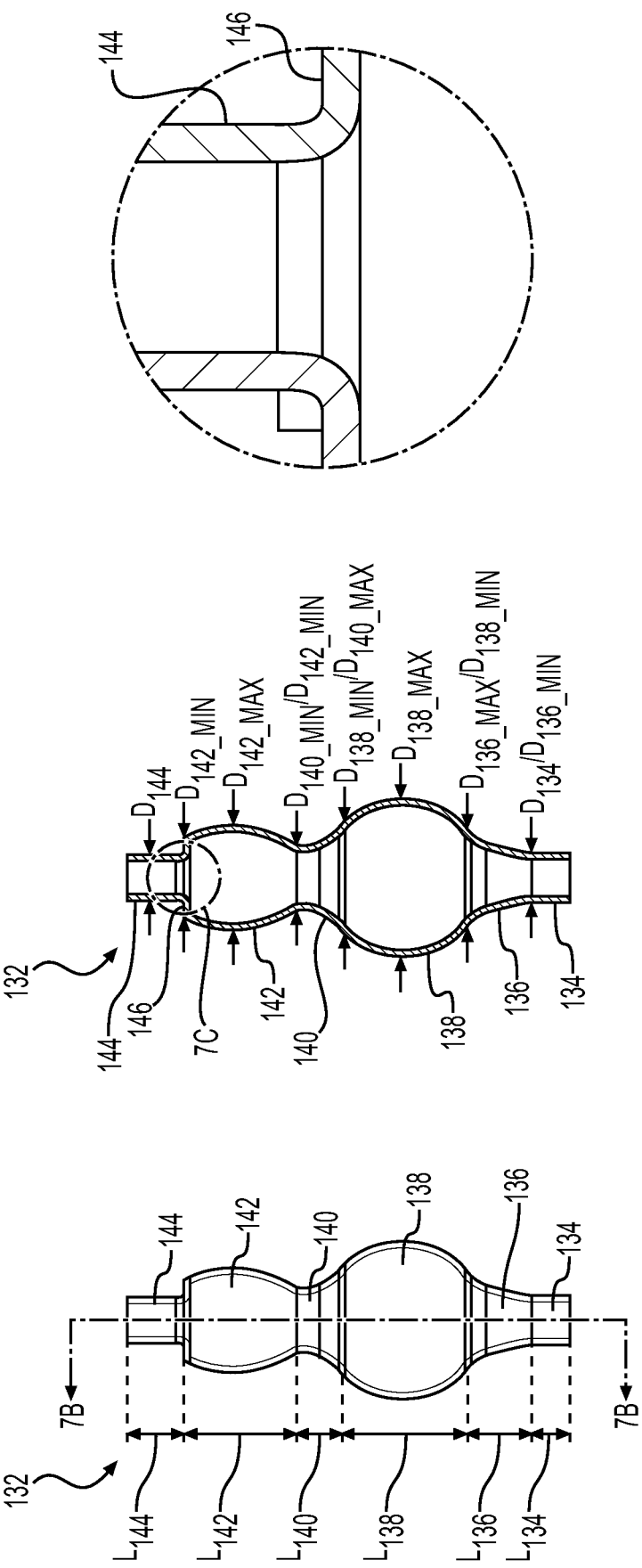

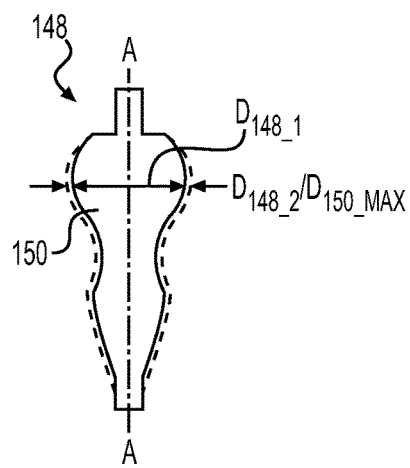
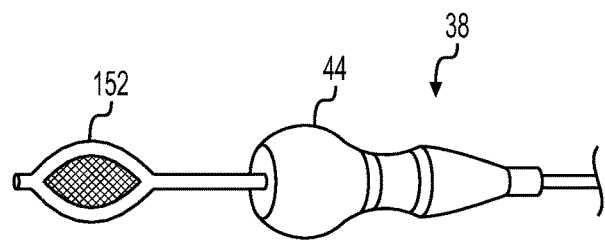
FIG. 9         FIG. 10
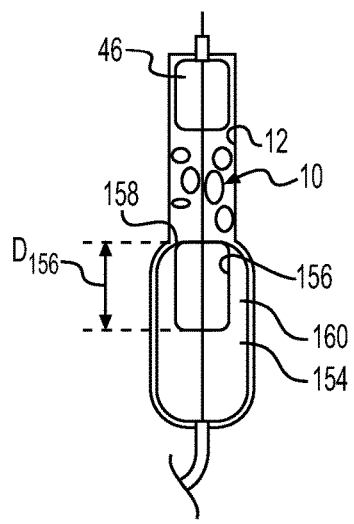   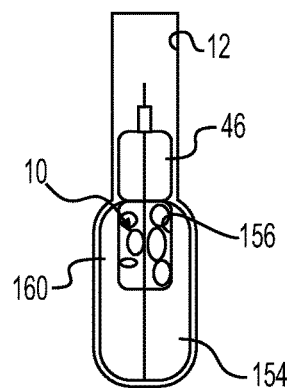   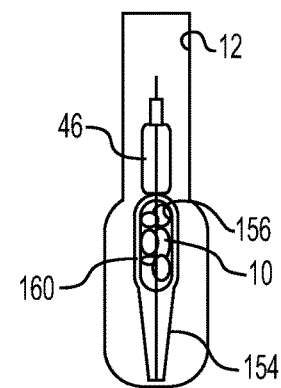
FIG. 11A      FIG. 11B      FIG. 11C

MEDICAL INSTRUMENT HAVING A BALLOON AND AN EXTRACTION MEMBER

CROSS-REFERENCE TO RELATED APPLICATIONS

This application claims the benefit of priority from U.S. Provisional Application No. 63/006,793, filed on Apr. 8, 2020, which is incorporated by reference herein in its entirety.

TECHNICAL FIELD

This disclosure relates generally to a medical instrument having a balloon and an extraction member. In examples, this disclosure is directed to a medical instrument and a related method for removing material from a subject using a dilation balloon and an extraction member.

BACKGROUND

During an endoscopic procedure to treat biliary lithiasis, such as a biliary endoscopic sphincterotomy (ES) procedure, operators may encounter problems when removing a material, such as a stone, from a bile duct of a subject. Operators often need to use many different types of devices during such procedures, particularly if the material proves difficult to remove. For example, extraction of a relatively large stone from the bile duct may be problematic when the size of the stone exceeds a size of the ampulla, which can inhibit extraction or cause complications during extraction. A biliary ES procedure may involve cutting of a biliary sphincter and an intraduodenal segment of a common bile duct of a subject, following selective cannulation, using a high frequency current applied with a special knife, or a sphincterotome, inserted into a papilla. An ES procedure thus may require multiple devices and exchanging of the multiple devices throughout the ES procedure. In addition, complications may arise during or as a result of the ES procedure, including damage to a sphincter mechanism of the subject.

SUMMARY

Aspects of the disclosure relate to, among other things, a medical instrument for removing a material from a subject using a dilation balloon and an extraction member, and a related method. Each of the aspects disclosed herein may include one or more of the features described in connection with any of the other disclosed aspects.

According to an example, a medical instrument includes a tube, a sheath provided around the tube and coaxial with the tube, and an inflatable balloon provided at a distal end of the sheath. The balloon is configured to receive a fluid from a lumen of the sheath, and has a central opening along a longitudinal axis thereof, and into which the tube extends, a proximal portion, a middle portion adjacent to and distal of the proximal portion, and a distal portion adjacent to and distal of the middle portion. In response to inflation, a maximum diameter of the middle portion is less than or equal to a maximum diameter of the proximal portion, and is less than a maximum diameter of the distal portion. The medical instrument also includes an extraction member provided at a distal end of the tube, distal to the balloon, and movable axially relative to the balloon.

Any of the medical devices described herein may also include one or more of the following features. A distal end of the sheath may be positioned within the central opening of the balloon. The extraction member may have a central opening along a longitudinal axis thereof, into which the tube extends. The extraction member may be one of a balloon, configured to receive a fluid from a lumen of the tube, and a net. The proximal portion of the balloon may include a proximal tapered portion. The proximal portion of the balloon may include a spherical distal portion and a proximal tapered portion. The distal portion of the balloon may be cylindrical with respect to a longitudinal axis thereof. The distal portion of the balloon may be spherical with respect to the longitudinal axis thereof. The maximum diameter of the proximal portion may be equal to the maximum diameter of the middle portion of the balloon. The maximum diameter of the proximal portion may be less than the maximum diameter of the distal portion of the balloon. A length of the proximal portion of the balloon may be greater than each of a length of the distal portion and a length of the middle portion of the balloon, with respect to a longitudinal axis of the balloon, and the length of the middle portion may be less than or equal to the length of the distal portion. The tube may include a distal opening, and a lumen of the tube may be configured to receive a guidewire that can extend past the distal opening of the tube. A distal facing surface of the distal portion of the balloon may be concave. A distal facing surface of the distal portion of the balloon may define a recess extending radially inward and proximally toward the middle portion of the balloon. The recess may extend proximally to a depth that is less than or equal to one-half of a longitudinal length of the distal portion of the balloon.

According to another example, a medical instrument includes a tube, a sheath provided around the tube and coaxial with the tube, and a balloon provided at a distal end of the sheath. The balloon is configured to be inflated via a lumen of the sheath, and has a distal facing concave surface. In response to inflation, the balloon has an hourglass shape. The medical instrument also includes an extraction member provided at the distal end of the tube, distal to the balloon.

Any of the medical devices described herein may also include one or more of the following features. The hourglass shape may be defined by a proximal bulb portion, a middle neck portion, and a distal bulb portion. The distal surface of the distal bulb portion of the balloon may define a recess extending radially inward and proximally toward the proximal bulb portion of the balloon, the recess being configured to house a biliary stone.

According to still another example, a method of removing material from a subject includes advancing a device into a lumen of the subject, the device including a tube, a sheath provided around the tube and coaxial with the tube, and a dilation balloon provided at a distal end of the device. The dilation balloon has a central opening along a longitudinal axis thereof, the central opening receiving the tube, a proximal portion, a middle portion adjacent to and distal of the proximal portion, and a distal portion adjacent to and distal of the middle portion. The devices also includes an extraction member provided at a distal end of the tube, and distal of the dilation balloon. The method further includes positioning the extraction member distally of the material, positioning the dilation balloon proximally of the material, inflating the dilation balloon so that a maximum diameter of the middle portion of the dilation balloon is less than or equal to a maximum diameter of the proximal portion of the dilation balloon, and less than a maximum diameter of the distal portion of the balloon, and pulling at least the extraction member proximally to pull the material proximally.

Any of the methods described herein may also include one or more of the following features. The extraction member may include an extraction balloon. In addition, the method may further include inflating the extraction balloon before or after the inflating of the dilation balloon.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIGS. 5A-5D show a perspective view, a side view, a cross-sectional view, and a detail cross-sectional view, respectively, of a dilation balloon, according to an embodiment of the disclosure.

FIGS. 6A-6C show a side view, a cross-sectional view, and a detail cross-sectional view, respectively, of a dilation balloon, according to another embodiment of the disclosure.

FIGS. 7A-7C show a side view, a cross-sectional view, and a detail cross-sectional view, respectively, of a dilation balloon, according to still another embodiment of the disclosure.

FIG. 9 shows a side view of a dilation balloon, according to yet another embodiment of the disclosure.

FIG. 10 shows a side view of a medical instrument having a dilation balloon and a net, according to another embodiment of the disclosure.

FIGS. 11A-11C show a medical instrument having a dilation balloon with a recess, according to a further embodiment of the disclosure.

DETAILED DESCRIPTION

It may be understood that both the foregoing general description and the following detailed description are exemplary and explanatory only, and are not restrictive of the invention, as claimed. As used herein, the terms "comprises," "includes," "has," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the terms "proximal" or "proximally" mean a direction closer to an operator, and the terms "distal" or "distally" mean a direction further from an operator. As used herein, the terms "about," "substantially," and "approximately," indicate a range of values within +/−10% of a stated value. Although endoscopes and endoscopic procedures are referenced herein, references to endoscopes and endoscopic procedures should not be construed as limiting the possible applications of the disclosed medical instruments and other aspects, and the disclosed medical instruments and portions thereof may be used as portions of other types of medical devices and in other types of medical procedures.

Figure 1:
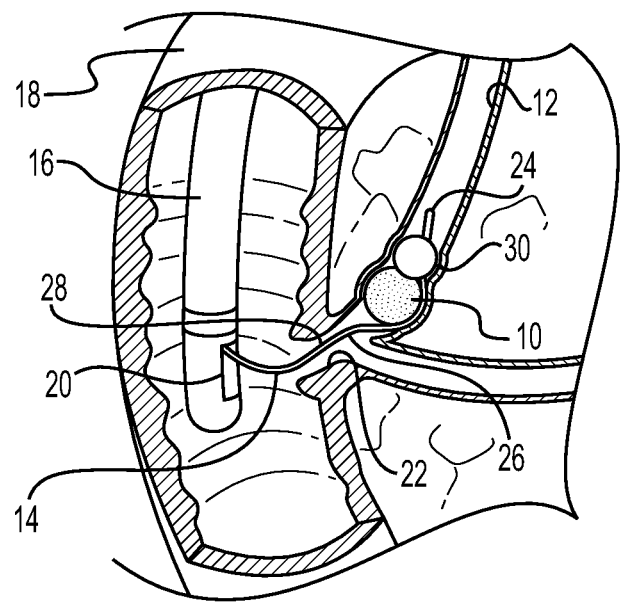
FIG. 1 shows a schematic view of a portion of a medical instrument extending through a duodenum and into a bile duct of a subject.

As an alternative to an ES procedure described above, an endoscopic papillary balloon dilation (EPBD) procedure may be performed, which may minimize complications and preserve the sphincter mechanism. For example, as shown in FIG. 1, a material 10, such as a stone, may be located within a bile duct 12 of a subject, and may be removed in an EPBD procedure using a medical instrument 14. During the procedure, the medical instrument 14 is advanced distally through a duodenoscope 16 (or other scope, catheter, sheath, or tube) that is positioned within a gastrointestinal tract of the subject. More specifically, the duodenoscope 16 is positioned within a duodenum 18 of the subject, and has a distal opening 20 positioned to face a papilla, here, an ampulla of Vater 22. Within the opening may 20 may be an elevator (unshown) to lift and direct the medical instrument to the side of duodenoscope 16. The medical instrument 14 extends from the distal opening 20, through the ampulla of Vater 22, and into the bile duct 12, over a guidewire 24. A portion of the medical instrument 14 that extends into the bile duct 12 is a treatment portion 26. The treatment portion 26 includes a lumen 28 and an extraction member 30. The extraction member 30 is provided toward a distal end of the treatment portion 26. During the endoscopic procedure, the extraction member 30 is positioned distally of the material 10, and is expandable and/or inflatable with a fluid through an opening (unshown) in the lumen 28.

To remove the material 10 from the bile duct 12, the extraction member 30 is pulled proximally, i.e., trawled, through the bile duct 12. During this process, in a case in which the extraction member 30 is a balloon, a force needed to pull the material 10 out of the bile duct 12 may cause the extraction balloon 30 to burst. In addition, in a case in which the bile duct 12 of the subject is a "sigmoid" bile duct, e.g. curved or crescent-shaped, the medical instrument 14 may require torqueing by an operator performing the procedure, which requires additional strength and endurance on the part of the operator, and increases aggravation to the bile duct 12 and other lumens of the subject.

In order to reduce the force needed to pull the material 10 out of the bile duct 12, and thus reduce the risk of bursting of the extraction balloon 30, a lumen on a proximal side of the material 10 may be dilated. To that end, an additional instrument may be needed, including an additional lumen or sheath and a dilation balloon at a distal end thereof. The dilation balloon is positioned on a proximal side of the material 10 within the bile duct 12. In order to remove the material 10 while preserving the sphincter mechanism, the extraction member 30 and the dilation balloon may be moved simultaneously in the proximal direction.

Problems may arise, however, when multiple devices or instruments are needed to trawl the bile duct 12 and to dilate the ampulla of Vater 22. For example, the instruments may become tangled during insertion or exchanging thereof. Further, as the instruments are exchanged or moved relative to each other, the guidewire 24 may move, and, as a result, the operator may lose access to the bile duct 12, requiring recannulation. This process may cause additional aggravation of the ampulla of Vater of the subject. Further, the use of multiple instruments increases a cost of the endoscopic procedure, as well as the time needed to complete the endoscopic procedure. The increased time needed to complete the endoscopic procedure, in turn, may increase the invasiveness of the procedure, the aggravation to the gastrointestinal tract of the subject, and a risk to the subject for infection or injury.

Figure 2:
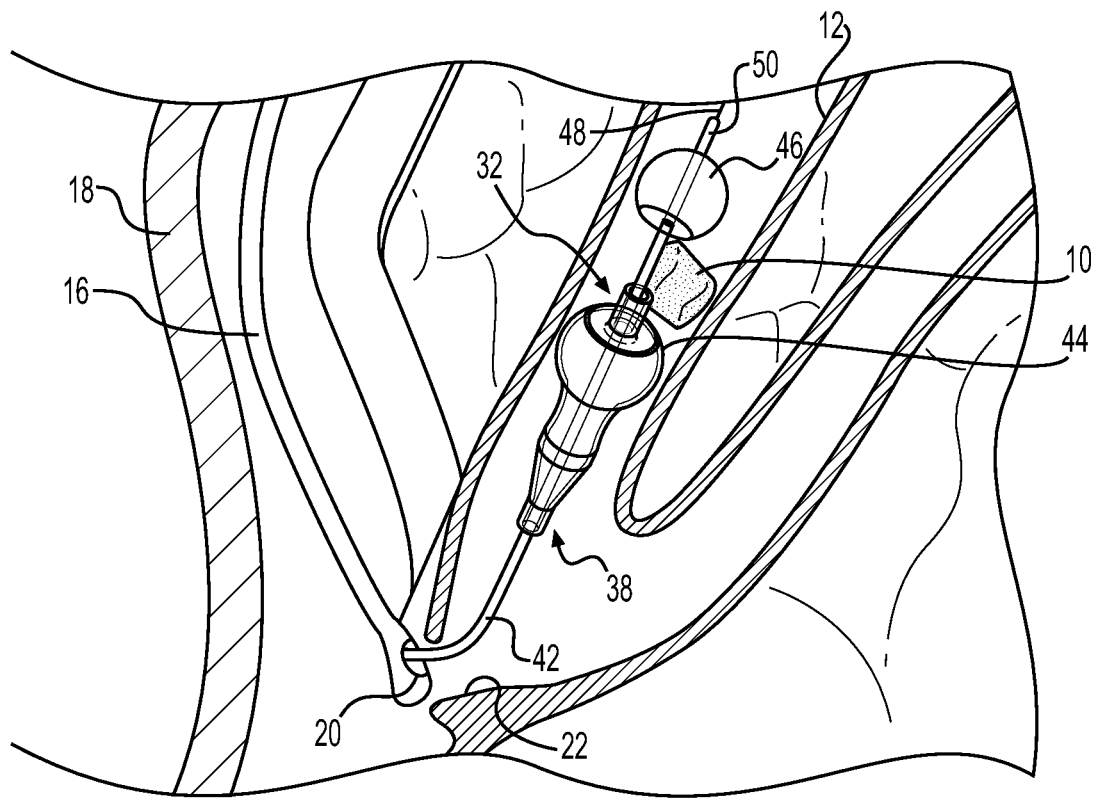
FIG. 2 shows a schematic view of a portion of a medical instrument, according to the disclosure, extending through the duodenum and into the bile duct of the subject.

FIG. 2 shows a schematic view of a portion of a medical instrument 32 according to an example of the disclosure. The medical instrument 32 is positioned within a duodenoscope 16 (or other scope, catheter, sheath, or tube), which is positioned within a duodenum 18 of a subject, during an endoscopic procedure. The medical instrument 32 extends through the duodenoscope 16, out of a distal opening 20 of the duodenoscope 16, through an ampulla of Vater 22, and into a bile duct 12 of the subject. A treatment portion 38 of the medical instrument 32 extends into the bile duct 12, to a position around or near a material 10 to be extracted from the bile duct 12. The treatment portion 38 includes a tube 40 (shown in FIG. 3) and a sheath 42 extending coaxially around the tube 40 and movable relative to the tube 40. The treatment portion 38 also includes a dilation balloon 44 and an extraction member 46, each of which is shown in an expanded state in FIG. 2. In the embodiment shown in FIGS. 1 and 2, the extraction member 46 is a balloon. The extraction member 46 may, however, be any suitable feature for capturing and moving an object for retrieval, such as a net shown in FIG. 10. The dilation balloon 44 and the extraction member 46 can be expanded and moved independently of each other, as the dilation balloon 44 is mounted to the sheath and the extraction member 46 is mounted to the tube 40. The dilation balloon 44 can be moved by moving the sheath 42 distally or proximally, while the extraction member 46 can be moved by moving the tube 40 distally or proximally. In addition, the dilation balloon 44 and the extraction member 46 may be expanded and moved simultaneously. As shown in FIG. 2, the dilation balloon 44 is positioned proximally of the material 10, and the extraction member 46 is positioned distally of the material 10. The treatment portion 38 may be advanced over a guidewire 48 to reach the position shown in FIG. 2. In addition, a distal tip 50 of the treatment portion 38 may form an atraumatic tip, and includes a distal opening 51 through which the guidewire 48 can pass.

Figure 3:
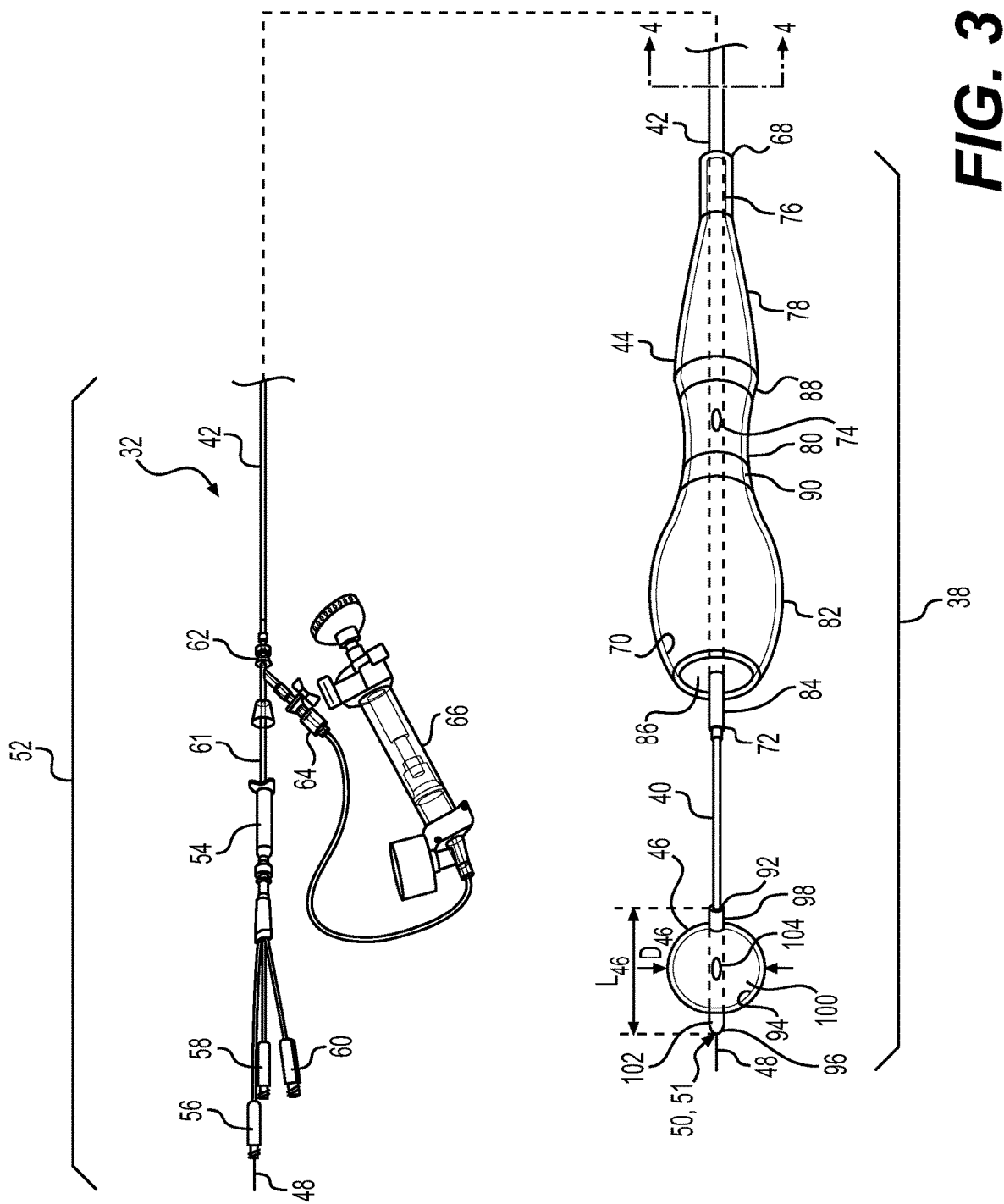
FIG. 3 shows a schematic view of a medical instrument, according to the disclosure.

FIG. 3 shows a schematic view of the medical instrument 32, according to an example of the disclosure. At a proximal end 52 of the medical instrument 32, the tube 40, which may be a tri-lumen extruded tube, is connected to a handle 54. The handle 54 includes a plurality of ports, including a guidewire port 56, a contrast port 58, and an extraction member expansion port 60. The guidewire port 56 receives the guidewire 48, the contrast port 58 receives a contrast material, such as a dye, from a contrast material supply (not shown) or receives another desired fluid, and the extraction member expansion port 60 receives a mechanism for expansion of the extraction member 46. For example, the extraction member expansion port 60 may receive a fluid, such as air or saline, from a fluid supply, such as a pump or a syringe (not shown), in a case in which the extraction member 46 is a balloon. The handle 54 also provides for co-axial movement of the dilation balloon 44 and the extraction member 46 relative to each other.

Distally of the handle 54, as shown in FIG. 3, a hypotube 61 and an adapter 62, such as a Tuohy Borst adapter, may be provided around the tube 40. The sheath 42 is connected to the adapter 62, and extends co-axially with and around the tube 40 from the adapter 62 toward the treatment portion 38 of the medical instrument 32. The adapter 62 includes a dilation balloon inflation port 64. The dilation balloon inflation port 64 receives a fluid, such as air or saline, from a fluid supply, such as a pump or a syringe 66, as shown in FIG. 3. The adapter 62 provides for co-axial movement of the handle 54 and the hypotube 61, and prevents leakage of the fluid back through the handle 54.

With reference to FIG. 3, the tube 40 and the sheath 42 extend co-axially from the proximal end 52 toward the distal tip 50 of the treatment portion 38 of the medical instrument 32. The sheath 42 extends through a proximal end 68 of the dilation balloon 44, through a central opening 70 of the dilation balloon 44, and terminates at or near a distal end 72 of the dilation balloon 44. The sheath 42 has a circumferential opening 74 that is positioned between the proximal end 68 and the distal end 72 of the dilation balloon 44.

The medical instrument 32 may have a length, from the proximal end 52 to the distal tip 50, of approximately 220 cm, for example. The length of the medical instrument 32 is not, however, limited to this value, and may vary within a range of approximately 200 cm to 240 cm. The tube 40 of the medical instrument 32 may have a length of approximately 220 cm and a diameter of approximately 3.0 mm. The length and the diameter of the tube 40 are not, however, limited to these values, and may vary within a range of approximately 200 cm to 240 cm and a range of approximately 2.5 mm to 3.5 mm, respectively. The tube 40 may be formed of a material, such as PEBAX®, for example. The material that forms the tube 40, is not, however, limited to PEBAX®, and may be any one of low-density polyethylene (LDPE), high-density polyethylene (HDPE), polyether ether ketone (PEEK), nylon, Cristamid, Grilamid®, polytetrafluoroethylene (PTFE), Zytel®, Rilsan®, or Vestamid®. In addition, semi-compliant materials may be used, including, for example, ethylene-vinyl acetate, polyvinyl chloride (PVC), olefin copolymers or homopolymers, polyethylenes, polyurethanes, cross-linked low density polyethylenes (PETs), highly irradiated linear low density polyethylene (LDPE), acrylonitrile polymers and copolymers, acrylonitrile blends and ionomer resins. Examples of non-compliant materials include polyethylene terephthalates, polyacrylenesulfide, and copolyesters. Still further, other examples of the material include Poly(Styrene-Isobutylene-Styrene) Triblock polymer (SIBS), polyurethane, an elastic polymer, woven fabric, a multi-walled membrane of polymer, and combinations thereof.

The sheath 42 of the medical instrument 32 may have a length of approximately 165 cm and a diameter of approximately 3.0 mm. The length and the diameter of the sheath 42 are not, however, limited to these values, and may vary within the ranges of approximately 145 cm to 185 cm and approximately 2.5 mm to 3.5 mm, respectively. The sheath 42 may be formed of a material, such as PEBAX®. The material that forms the sheath 42, is not, however, limited to PEBAX®, and may be any one of low-density polyethylene (LDPE), high-density polyethylene (HDPE), polyether ether ketone (PEEK), nylon, Cristamid, Grilamid®, polytetrafluoroethylene (PTFE), Zytel®, Rilsan®, or Vestamid®. In addition, semi-compliant materials may be used, including, for example, ethylene-vinyl acetate, polyvinyl chloride (PVC), olefin copolymers or homopolymers, polyethylenes, polyurethanes, cross-linked low density polyethylenes (PETs), highly irradiated linear low density polyethylene (LDPE), acrylonitrile polymers and copolymers, acrylonitrile blends and ionomer resins. Examples of non-compliant materials include polyethylene terephthalates, polyacrylenesulfide, and copolyesters. Still further, other examples of the material include Poly(Styrene-Isobutylene-Styrene) Triblock polymer (SIBS), polyurethane, an elastic polymer, woven fabric, a multi-walled membrane of polymer, and combinations thereof.

In the embodiment shown in FIG. 3, the dilation balloon 44 has an hourglass shape, which allows for controlled dilation of the bile duct 12 and the ampulla of Vater 22 during an endoscopic procedure, as discussed below. In particular, from the proximal end 68 to the distal end 72, the dilation balloon 44 includes a proximal neck 76, a proximal portion 78, a middle portion 80, a distal portion 82, and a distal neck 84. The dilation balloon 44 has a wall thickness of, for example, approximately 0.050 mm, which may be constant across the proximal neck 76, the proximal portion 78, the middle portion 80, the distal portion 82, and the distal neck 84. In the embodiment shown in FIG. 3, the shapes and diameters of the proximal neck 76, the proximal portion 78, the middle portion 80, the distal portion 82, and the distal neck 84 vary. The varying shapes and diameters of these portions of the dilation balloon 44 are discussed in more detail below, with respect to FIGS. 5A-7C.

The distal portion 82 of the dilation balloon has a distal facing surface 86, into which the material 10 may be moved when the medical instrument 32 is in use. In the embodiment shown in FIG. 3, the distal facing surface 86 is shown as a concave surface. The concavity of the distal facing surface 86 defines a space into which the material 10 may be captured or secured for removal, as discussed in more detail below. The distal facing surface 86 is not, however, limited to being a concave surface, and may be planar or convex, or may have a recess, as discussed below with respect to FIGS. 11A-11C. The central opening 70 of the dilation balloon 44 extends through the entire length of the dilation balloon 44. In addition, one or more marker bands may be provided on the dilation balloon 44. In the embodiment shown in FIG. 3, two marker bands are provided, with one marker band 88 positioned between the proximal portion 78 and the middle portion 80, and another marker band 90 positioned between the middle portion 80 and the distal portion 82 of the dilation balloon 44.

The dilation balloon 44 may be formed of nylon, for example. The material that forms the dilation balloon 44 is not, however, limited to nylon, and may be other materials, such as polyethylene terephthalate (PET), PEBAX®, or another suitable material. As noted above, the dilation balloon 44 may have varying shapes and diameters between the proximal neck 76, the proximal portion 78, the middle portion 80, the distal portion 82, and the distal neck 84, and may be formed using free forming. Other techniques may, however, be used to form the dilation balloon 44, such as stretch blowing, extruded blow molding. The dilation balloon 44 may be formed of a compliant material or a noncompliant material. Details of the varying shapes and diameters of the dilation balloon 44 are described in more detail below, with reference to FIGS. 5A-7C.

With reference to FIG. 3, distal of the dilation balloon 44, the tube 40 extends through a proximal end 92, through a central opening 94, and into a distal end 96 of the extraction member 46, which may terminate at and form the distal tip 50 of the treatment portion 38. In the case in which the extraction member 46 is a balloon, as shown in FIG. 3, the extraction member 46 has a proximal neck 98, a middle portion 100, and a distal neck 102. The tube 40 has a circumferential opening 104 that is positioned within the middle portion 100 of the extraction member 46. When in an inflated state, as shown in FIG. 3, the middle portion 100 of the extraction member 46 has an ovoid-shaped profile. A diameter D46 of the middle portion of the extraction member 46 may be, for example, approximately 11 mm, and a length L46 of the extraction balloon 46 may be, for example, approximately 11 mm. The diameter D46 and the length L46 of the extraction member 46 are not, however, limited to these values, and may be within the ranges of approximately 5 mm to 13 mm and approximately 5 mm to 13 mm, respectively.

In the case in which the extraction member 46 is a balloon, the extraction member 46 may be formed of nylon, for example. The material that forms the extraction member 46 is not, however, limited to nylon, and may be other materials, such as polyethylene terephthalate (PET), PEBAX®, or another suitable material. As noted above, the extraction member 46, as a balloon, may have an ovoid shape and particular diameters of the proximal neck 98, the middle portion 100, and the distal neck 102, and may be formed using free forming. Other techniques may, however, be used to form the extraction member 46, such as stretch blowing, extruded blow molding. The extraction member 46, as a balloon, may be formed of a compliant material or a noncompliant material.

Figure 4:
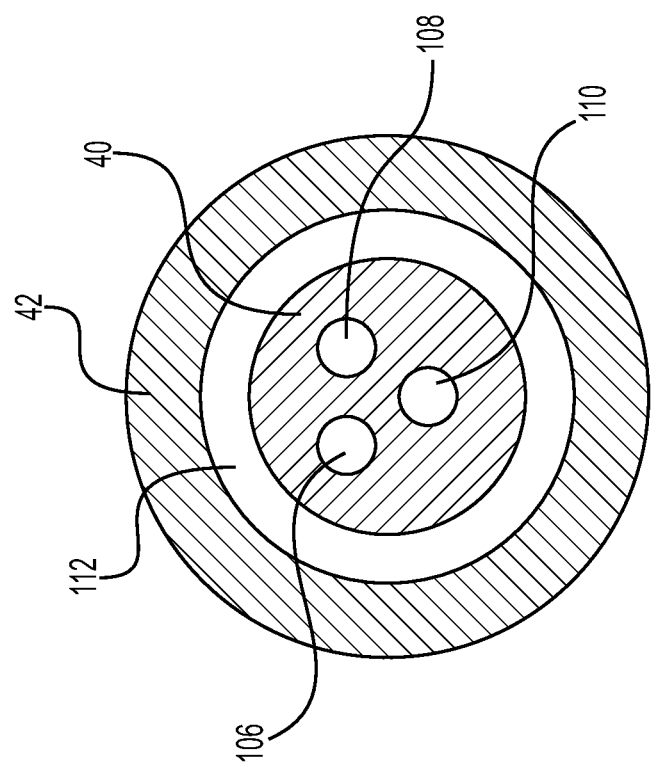
FIG. 4 shows a cross-sectional view of a tube and a sheath of the medical instrument of FIG. 3, according to the disclosure.

FIG. 4 shows a cross-sectional view of the tube 40 and the sheath 42, taken along section line 4-4 in FIG. 3. As shown in FIG. 4, the tube 40 has at least three lumens, including a guidewire lumen 106, a contrast lumen 108, and an extraction member expansion lumen 110. The guidewire lumen 106 receives the guidewire 48, which extends from the guidewire port 56 of the handle 54 and can extend through the distal tip 50 of the treatment portion 38 of the medical instrument 32. The contrast lumen 108 receives the contrast material from the contrast material supply (or other desired fluid) via the contrast port 58 in the handle 54. In addition, in the case in which the extraction member 46 is a balloon, the extraction member expansion lumen 110 receives the fluid for inflation of the extraction member 46 from the fluid supply via the extraction member expansion port 60. That is, the extraction member 46 is inflated when the fluid is supplied through the extraction member expansion lumen 110 and the circumferential opening 104 in the tube 40. Further, a dilation balloon inflation lumen 112 is formed between an outer circumferential surface of the tube 40 and an inner circumferential surface of the sheath 42, and is connected to the dilation balloon inflation port 64. The dilation balloon inflation lumen 112 receives the fluid for inflation of the dilation balloon 44 from the syringe 66, shown in FIG. 3. That is, the dilation balloon 44 is inflated when the fluid is supplied through the dilation balloon inflation lumen 112 and the circumferential opening 74 in the sheath 42.

With reference to FIG. 3, in the case in which the extraction member 46 is a balloon, the proximal neck 98 and the distal neck 102 of the extraction member 46 form a tight fit around the tube 40, thereby preventing the fluid received from the extraction member expansion lumen 110 from leaking out of the extraction member 46. Similarly, the proximal neck 76 and the distal neck 84 of the dilation balloon 44 form a tight fit around the sheath 42, in a case in which the sheath 42 terminates beyond the distal end 72 of the dilation balloon 44, thereby preventing the fluid received from the dilation balloon inflation lumen 112 from leaking out of the dilation balloon 44. And, in a case in which the sheath 42 terminates proximal to the distal end 72 of the dilation balloon 44, the distal neck 84 of the dilation balloon 44 forms a tight fit around the tube 40, thereby preventing the fluid received from the dilation balloon inflation lumen 112 from leaking out of the dilation balloon 44. In addition, the proximal neck 98 of the extraction member 46 and the distal neck 84 of the dilation balloon 44 form robust stop sleeves to prevent excessive withdrawal of the extraction member 46 into the dilation balloon 44.

Figure 5A:
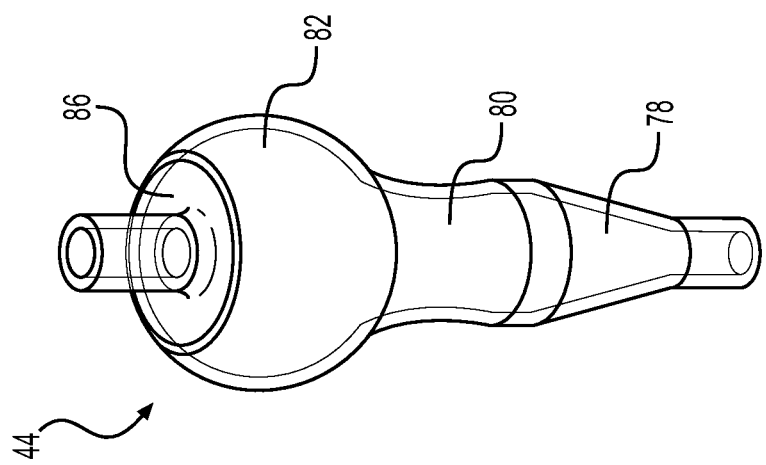

FIGS. 5A-5D show additional details of the dilation balloon 44 according to an embodiment of the disclosure. FIG. 5A shows a perspective view of the dilation balloon 44, which has an hourglass shape, defined by the proximal portion 78, the middle portion 80, and the distal portion 82. The distal portion 82 may be spherical or bulb-shaped. FIG. 5A also shows the distal facing surface 86 of the dilation balloon 44. FIG. 5B is a side view of the dilation balloon 44, and shows the respective lengths of the proximal neck 76, the proximal portion 78, the middle portion 80, the distal portion 82, and the distal neck 84. That is, the proximal neck 76 has a length L76, the proximal portion 78 has a length L78, the middle portion 80 has a length L80, the distal portion 82 has a length L82, and the distal neck 84 has a length L84. The relationships between the lengths of the proximal neck 76, the proximal portion 78, the middle portion 80, the distal portion 82, and the distal neck 84 may be as follows: L76<L84<L80=L82<L78. The relationships between the lengths of the proximal neck 76, the proximal portion 78, the middle portion 80, the distal portion 82, and the distal neck 84 are not, however, limited to these relationships, and may vary.

FIG. 5C is a cross-sectional view of the dilation balloon 44 taken along line 5C-5C in FIG. 5B. In this embodiment, the proximal neck 76 and the distal neck 84 have approximately constant diameters D76 and D84, respectively, while the proximal portion 78, the middle portion 80, and the distal portion 82 may have varying diameters across their respective lengths. That is, the proximal portion 78 may have a proximal portion maximum diameter D78_MAX of approximately 20 mm and a proximal portion minimum diameter D78_MIN of approximately 10 mm, the middle portion 80 may have a middle portion maximum diameter D80_MAX of approximately 18 mm and a middle portion minimum diameter D80_MIN of approximately 8 mm, and the distal portion 82 may have a distal portion maximum diameter D82_MAX of approximately 20 mm and a distal portion minimum diameter D82_MIN of approximately 10 mm, for example. The respective diameters of the proximal neck 76, the proximal portion 78, the middle portion 80, the distal portion 82, and the distal neck 84 of the dilation balloon 44 are not, however, limited to these respective values, and may vary.

As shown in FIG. 5C, the proximal portion 78 may have a tapered profile, with the proximal portion minimum diameter D78_MIN at a proximal end thereof, closest to the proximal neck 76, and the proximal portion maximum diameter D78_MAX near a distal end thereof, closest to the middle portion 80. The middle portion 80 may have a curved biconcave profile, forming a neck of the dilation balloon 44, with the middle portion minimum diameter D80_MIN at a center thereof, and the middle portion maximum diameter D80_MAX at each of a proximal end and a distal end thereof. In addition, the distal portion 82 may be spherical or shaped like a bulb, with a curved biconvex profile, with the distal portion minimum diameter D82_MIN at a proximal end thereof, and the distal portion maximum diameter D82_MAX at a center thereof. The outer circumferential surface of the dilation balloon 44 may be continuous and smooth across at least the proximal portion 78, the middle portion 80, and the distal portion 82.

In the embodiment shown in FIG. 5C, the relationships between the diameters of the proximal neck 76, the proximal portion 78, the middle portion 80, the distal portion 82, and the distal neck 84 may be as follows: D76= D84= D78_MIN<D80_MIN<D78_MAX=D80_MAX=D82_MIN<D82_MAX. That is, when the dilation balloon 44 is inflated, the distal portion maximum diameter D82_MAX is greater than the middle portion maximum diameter D80_MAX, and the middle portion maximum diameter D80_MAX is less than or equal to the proximal portion maximum diameter D78_MAX. The relationships between the diameters of the proximal neck 76, the proximal portion 78, the middle portion 80, the distal portion 82, and the distal neck 84 are not, however, limited to these relationships, and may vary. In a case in which the middle portion maximum diameter D80_MAX is less than the distal portion maximum diameter D82_MAX and the proximal portion maximum diameter D78_MAX, the middle portion 80 of the dilation balloon 44 forms an anchor that reduces the potential for the dilation balloon 44 to slip into or out of the ampulla of Vater 22 during the endoscopic procedure.

FIG. 5D is a detail view of the distal facing surface 86 of the dilation balloon 44. In particular, FIG. 5D shows an angle θ between the distal surface 86 and the distal neck 84 of the dilation balloon 44. The angle θ may be an acute angle, and, more specifically, may be between approximately 80° to 85°, for example. That is, in the embodiment shown in FIGS. 5A-5D, the distal surface 86 is concave with respect to the distal portion 82 of the dilation balloon 44. The distal surface 86 is not, however, limited to being a concave surface, and may be planar or convex, or may include a recess, as described below with reference to FIGS. 11A-11C.

FIGS. 6A-6C show a dilation balloon 114 according to an alternative embodiment of the disclosure. FIG. 6A is a side view of the dilation balloon 114, which includes a proximal neck 116, a proximal portion 118, a middle portion 120, a distal portion 122, and a distal neck 124. FIG. 6A also shows the respective lengths of the proximal neck 116, the proximal portion 118, the middle portion 120, the distal portion 122, and the distal neck 124. That is, the proximal neck 116 has a length L116, the proximal portion 118 has a length L118, the middle portion 120 has a length L120, the distal portion 122 has a length L122, and the distal neck 124 has a length L124. The relationships between the lengths of the proximal neck 116, the proximal portion 118, the middle portion 120, the distal portion 122, and the distal neck 124 may be as follows: L116<L124<L118=L120=L122. The relationships between the diameters and the lengths of the proximal neck 116, the proximal portion 118, the middle portion 120, the distal portion 122, and the distal neck 124 are not, however, limited to these relationships, and may vary.

FIG. 6B is a cross-sectional view of the dilation balloon 114, taken along line 6B-6B of FIG. 6A. In this embodiment, the proximal neck 116 and the distal neck 124 have constant diameters D116 and D124, respectively, while the proximal portion 118, the middle portion 120, and the distal portion 122 may have varying diameters across their respective lengths. That is, the proximal portion 118 may have a proximal portion maximum diameter D118_MAX of approximately 20 mm and a proximal portion minimum diameter D118_MIN of approximately 20 mm, the middle portion 120 may have a middle portion maximum diameter D120_MAX of approximately 18 mm and a middle portion minimum diameter D120_MIN of approximately 8 mm, and the distal portion 122 may have a distal portion maximum diameter D122_MAX of approximately 20 mm and a distal portion minimum diameter D122_MIN of approximately 10 mm, for example. The respective diameters of the proximal neck 116, the proximal portion 118, the middle portion 120, the distal portion 122, and the distal neck 124 of the dilation balloon 114 are not, however, limited to these respective values, and may vary.

Similarly to the dilation balloon 44 of the embodiment shown in FIGS. 5A-5D, the proximal portion 118 of the dilation balloon 114 shown in FIGS. 6A-6C may have a tapered profile, with the proximal portion minimum diameter D118_MIN at a proximal end thereof, closest to the proximal neck 116, and the proximal portion maximum diameter D118_MAX near a distal end thereof, closest to the middle portion 120. The middle portion 120 may have a curved biconcave profile, forming a neck of the dilation balloon 114, with the middle portion minimum diameter D120_MIN at a center thereof, and the middle portion maximum diameter D120_MAX at each of a proximal end and a distal end thereof.

In contrast to the embodiment shown in FIGS. 5A-5D, the distal portion 122 of the dilation balloon 114 shown in FIGS. 6A-6C may include a semi-spherical portion 126, with a curved profile, at a proximal end thereof, and cylindrical portion 128, with a straight profile, at a distal end thereof. The distal portion minimum diameter D122_MIN is at the proximal end of the semi-spherical portion 126 of the distal portion 122, and the distal portion maximum diameter D122_MAX is constant along the cylindrical portion 128 of the distal portion 122. The distal portion 122 also has a distal facing surface 130, which in this embodiment is a concave surface with respect to the distal portion 122. The outer circumferential surface of the dilation balloon 114 may be continuous and smooth across at least the proximal portion 118, the middle portion 120, and the distal portion 122.

In the embodiment shown in FIGS. 6A-6C, the relationships between the diameters of the proximal neck 116, the proximal portion 118, the middle portion 120, the distal portion 122, and the distal neck 124 may be as follows: D116=D124=D118_MIN<D120_MIN<D118_MAX= D120_MAX=D122_MIN<D122_MAX. The relationships between the diameters of the proximal neck 116, the proximal portion 118, the middle portion 120, the distal portion 122, and the distal neck 124 are not, however, limited to these relationships, and may vary.

FIG. 6C is a detail view of the distal facing surface 130 of the dilation balloon 114. In particular, FIG. 6C shows an angle A between the distal surface 130 and the distal neck 124 of the dilation balloon 114. The angle A may be an acute angle, and, more specifically, may be between approximately 80° to 85°, for example. That is, in the embodiment shown in FIGS. 6A-6C, the distal surface 130 is concave with respect to the distal portion 122 of the dilation balloon 114. The distal surface 130 is not, however, limited to being a concave surface, and may be planar or convex, or may include a recess, as described below with reference to FIGS. 11A-11C.

FIGS. 7A-7C show a dilation balloon 132 according to yet another embodiment of the disclosure. FIG. 7A is a side view of the dilation balloon 132, which includes a proximal neck 134, a proximal tapered portion 136, a proximal biconvex portion 138, a middle portion 140, a distal portion 142, and a distal neck 144. The proximal biconvex portion 138 may be spherical or bulb-shaped, and the middle portion 140 may form a curved neck of the dilation balloon 132. In addition, the distal portion 142 may be spherical or bulb-shaped. FIG. 7A also shows the respective lengths of the proximal neck 134, the proximal tapered portion 136, the proximal biconvex portion 138, the middle portion 140, the distal portion 142, and the distal neck 144. That is, the proximal neck 134 has a length L134, the proximal tapered portion 136 has a length L136, the proximal biconvex portion 138 has a length L138, the middle portion 140 has a length L140, the distal portion 142 has a length L142, and the distal neck 144 has a length L144. The relationships between the lengths of the proximal neck 134, the proximal tapered portion 136, the proximal biconvex portion 138, the middle portion 140, the distal portion 142, and the distal neck 144 may be as follows: L134<L140<L144<L136 <L142<L138. The relationships between the lengths of the proximal neck 134, the proximal tapered portion 136, the proximal biconvex portion 138, the middle portion 140, the distal portion 142, and the distal neck 144 are not, however, limited to these relationships, and may vary.

FIG. 7B is a cross-sectional view of the dilation balloon 132, taken along line 7B-7B of FIG. 7A. In this embodiment, the proximal neck 134 and the distal neck 144 have constant diameters D134 and D144, respectively, while the proximal tapered portion 136, the proximal biconvex portion 138, the middle portion 140, and the distal portion 142 may have varying diameters across their respective lengths. That is, the proximal tapered portion 136 may have a proximal tapered portion maximum diameter D136_MAX of approximately 8 mm and a proximal tapered portion minimum diameter D136_MIN of approximately 6 mm, the proximal biconvex portion 138 may have a proximal biconvex portion maximum diameter D138_MAX of approximately 20 mm and a proximal biconvex portion minimum diameter D138_MIN of approximately 10 mm, the middle portion 140 may have a middle portion maximum diameter D140_MAX of approximately 18 mm and a middle portion minimum diameter D140_MIN of approximately 8 mm, and the distal portion 142 may have a distal portion maximum diameter D142_MAX of approximately 20 mm and a distal portion minimum diameter D142_MIN of approximately 10 mm, for example. The diameters of the proximal neck 134, the proximal tapered portion 136, the proximal biconvex portion 138, the middle portion 140, the distal portion 142, and the distal neck 144 of the dilation balloon 132 are not, however, limited to these respective values, and may vary.

Similarly to the dilation balloon 44 and the dilation balloon 114 of the embodiments shown in FIGS. 5A-5D and 6A-6C, respectively, the proximal tapered portion 136 of the dilation balloon 132 may have a tapered profile, with the proximal tapered portion minimum diameter D136_MIN at a proximal end thereof, closest to the proximal neck 134, and the proximal portion tapered maximum diameter D136_MAX near a distal end thereof, closest to the proximal biconvex portion 138. In contrast to the dilation balloon 44 and the dilation balloon 114 of the previously described embodiments, however, the dilation balloon 132 has the proximal biconvex portion 138 between the proximal tapered portion 136 and the middle portion 140. The proximal biconvex portion 138 may have a spherical shape, with a biconvex profile. Each of the proximal end and the distal end of the proximal biconvex portion 138 may have the proximal biconvex portion minimum diameter D138_MIN, and the center of the proximal biconvex portion 138 may have the proximal biconvex portion maximum diameter D138_MAX, as shown in FIG. 7B. The middle portion 140 may have a curved tapered profile, with the middle portion maximum diameter D140_MAX at a proximal end thereof, closest to the proximal tapered portion 136, and the middle portion minimum diameter D140_MIN at a distal end thereof, closest to the distal portion 142.

In addition, similarly to the embedment shown in FIGS. 5A-5D, the distal portion 142 of the dilation balloon 132 may have a curved biconvex profile. The distal portion minimum diameter D142_MIN is at each of the proximal end and the distal end thereof, and the distal portion maximum diameter D142_MAX is at a center thereof, as shown in FIG. 7B. The distal portion 142 also has a distal facing surface 146, which in this embodiment is a planar surface. The outer circumferential surface of the dilation balloon 132 may be continuous and smooth across at least the proximal tapered portion 136, the proximal biconvex portion 138, the middle portion 140, and the distal portion 142.

In the embodiment shown in FIG. 7B, the relationships between the diameters of the proximal neck 134, the proximal tapered portion 136, the proximal biconvex portion 138, the middle portion 140, the distal portion 142, and the distal neck 144 may be as follows: D134=D144=D136_MIN<D136_MAX=D138_MIN=D140_MIN=D142_MIN<D142_MAX<D138_MIN=D140_MAX<D138_MAX. That is, in contrast to the embodiments shown in FIGS. 5A-5D and 6A-6C, the portion of the dilation balloon 132 having the greatest diameter is the proximal biconvex portion 138, rather than the distal portion 142. The relationships between the diameters the proximal neck 134, the proximal tapered portion 136, the proximal biconvex portion 138, the middle portion 140, the distal portion 142, and the distal neck 144 are not, however, limited to these relationships, and may vary.

FIG. 7C is a detail view of the distal facing surface 146 of the dilation balloon 132. In particular, FIG. 7C shows a right angle formed between the distal surface 146 and the distal neck 144 of the dilation balloon 132. That is, in the embodiment shown in FIGS. 7A-7C, the distal facing surface 146 is perpendicular to the outer circumferential surface of the distal neck 144 of the dilation balloon 132. Although the distal facing surface 146 is shown as a planar surface, the distal facing surface 146 is not so limited, and may be curved, concave, or convex, and may include a recess.

Figure 8:
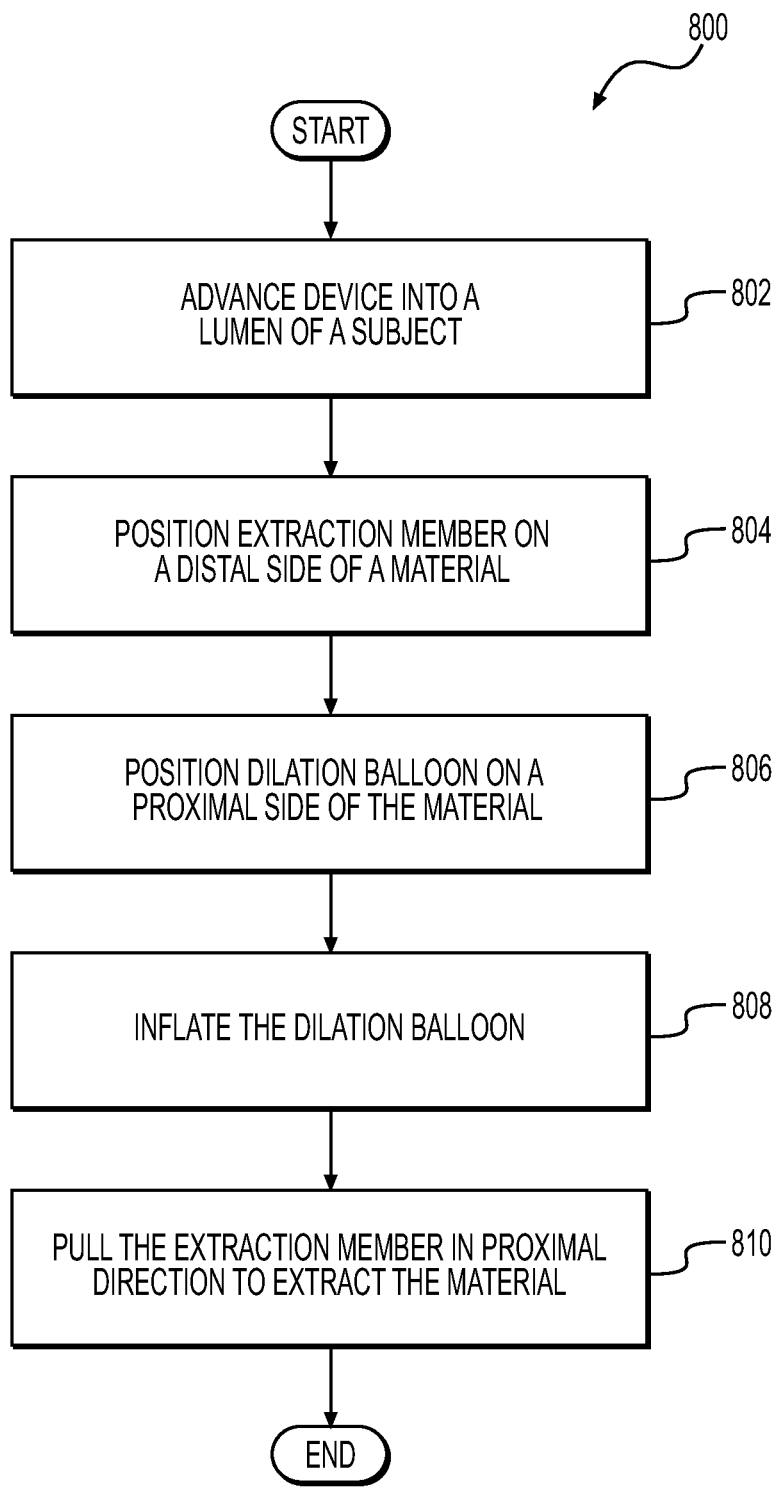
FIG. 8 shows a method of removing material from a subject, according to the disclosure.

FIG. 8 shows a method 800 of using the medical instrument 32 during an endoscopic procedure. In step 802, the medical instrument 32 is advanced into a lumen, such as the duodenum 18, of a subject. In this step, the medical instrument 32 may be advanced within the duodenoscope 16, positioned within the duodenum 18 of a gastrointestinal tract of the subject. The distal opening 20 of the duodenoscope 16 may be positioned so as to face the ampulla of Vater 22. The guidewire 48 may be advanced through the medical instrument 32, the distal opening 20, and the ampulla of Vater 22, and into the bile duct 12. The treatment portion 38 of the medical instrument 32 (in a deflated, contracted state) may be advanced over the guidewire 48 to be positioned in the bile duct 12, as shown in FIG. 2.

Then, in step 804, the extraction member 46, here, a balloon, is positioned beyond a distal side of the material 10, as shown in FIG. 2. In step 806, the dilation balloon 44 is positioned on a proximal side of the material 10, as shown in FIG. 2. In step 808, the dilation balloon 44 is inflated. In step 810, the extraction member 46 is pulled proximally (i.e., a direction back towards the duodenum 18), to extract the material 10 from the bile duct 12. In this step, the material 10 may be sandwiched between the extraction member 46 and the distal facing surface 86 of the dilation balloon 44. That is, while the extraction member 46 is pulled proximally, the dilation balloon 44 may remain stationary for a period of time, with the material 10 being pressed into a space defined by the concave distal facing surface 86, until the material 10 is sandwiched and secured between the extraction member 46 and the dilation balloon 44. The dilation balloon 44 and the extraction member 46 are movable separately from each other by virtue of the dilation balloon 44 being mounted to the sheath 42 and the extraction member 46 being mounted to the tube 40, with the sheath 42 being movable relative to the tube 40. In addition, the dilation balloon 44 and the extraction member 46 are inflatable separately from each other by virtue of the circumferential opening 74 of the sheath 42, through which fluid passes to inflate the dilation balloon 44, and the circumferential opening 104 of the tube 40, through which fluid passes to inflate the extraction member 46.

Then, the treatment portion 38 (including the extraction member 46 and the dilation balloon 44) may be withdrawn from bile duct 12. In an embodiment, the duodenoscope 16 and the instrument 32 may then be removed together from the subject. In another embodiment, all or a portion of instrument 32 may be pulled back into the duodenoscope 16 through the distal opening 20, and the medical instrument 32, including the removed material 10, may then be removed from the subject.

Although the method 800 is described as including steps 802 to 810, the method 800 may include additional steps. For example, the method 800 may include a step of cannulating the bile duct 12 and positioning the guidewire 48 therein, advancing the medical instrument 32 into the duodenum 18 until the distal tip 50 of the medical instrument 32 is positioned against the ampulla of Vater 22, and advancing the treatment portion 38 over the guidewire 48 into the bile duct, before performing the step 804 of positioning the extraction member 46 on a distal side of the material 10.

In addition, in a case in which the extraction member 46 is a balloon, the method 800 may also include an additional step of inflating the extraction member 46. The step of inflating the extraction member 46 may be performed after step 804, in which the extraction member 46 is positioned beyond the distal side of the material, before, at the same time as, or after step 808, in which the dilation balloon 44 is inflated. The method 800 may also include a step of withdrawing the material 10, sandwiched between the inflated extraction member 46 and the inflated dilation balloon 44, from the bile duct 12 and into the duodenum 18. The method 800 may also include a step of deflating the extraction member 46 and the dilation balloon 44, before withdrawing the material 10 into the duodenum 18.

In addition, in a case in which the material 10 is particularly difficult to move using the steps of the method 800 noted above, in an alternative embodiment, the method 800 may further include a step of deflating the dilation balloon 44, a step of moving the dilation balloon 44 proximally within the bile duct 12, and a step of then reinflating the dilation balloon 44. Then, the extraction member 46 may be pulled proximally to move the material 10 towards the dilation balloon 44. These steps may be repeated until the material 10 becomes free-moving or has been removed from the bile duct 12.

In an alternative embodiment, the dilation balloon 44 and the extraction member 46 may be expanded, or inflated, and moved simultaneously.

In another alternative embodiment, the method 800 may include a step of injecting contrast into the bile duct 12 via the contrast port 58 and the contrast lumen 108, to provide a fluoroscopic image of the material 10, as well as duct dimensions and complexity. In this alternative embodiment, the contrast may be injected before or after step 804, in which the extraction member 46 is positioned on a distal side of the material 10.

In yet another alternative embodiment, the method 800 may include a step of confirming a position of the dilation balloon 44 within the bile duct 12 using the marker bands 88 and 90. That is, the marker bands 88 and 90 may be used to confirm that middle portion 80 of the dilation balloon 44 is at least positioned within the ampulla of Vater 22, and the distal portion 82 of the dilation balloon 44 is at least positioned within the bile duct 12. The step of confirming the position of at least the middle portion 80 and the distal portion 82 of the dilation balloon 44 may be performed before the step 808 of inflating the dilation balloon 44.

In still another alternative embodiment, the method 800 may include an additional step, after inflating a dilation balloon 148 to a first or initial inflated diameter $D148\_1$ in step 808, of inflating the dilation balloon 148 to a second, or subsequent inflated diameter $D148\_2$, as shown in FIG. 9. In this alternative embodiment, if the material 10 is, for example, a large stone located in the bile duct, it may be necessary to further dilate the ampulla of Vater 22 in order to extract the stone from the bile duct 12. Accordingly, the dilation balloon 148 may be inflated to the first inflated diameter $D148\_1$ in step 808, and, before step 810, in which the extraction balloon 46 is pulled proximally, the dilation balloon 148 may be further inflated to the second inflated diameter $D148\_2$. The dilation balloon 148 of this embodiment may have the same structure as the dilation balloon 44 shown in FIGS. 5A-5D, the dilation balloon 114 shown in FIGS. 6A-6C, or the dilation balloon 132 shown in FIGS. 7A-7C. The dilation balloon 148 includes at least a distal portion 150 having the distal portion maximum diameter $D150\_MAX$. The first inflated diameter $D148\_1$ and the second inflated diameter $D148\_2$ may be defined with respect to the distal portion maximum diameter $D150\_MAX$ of the dilation balloon 148, i.e., across a center of a distal portion 150, as shown in FIG. 9, with respect to a longitudinal axis A-A of the dilation balloon 148.

In addition, in another alternative embodiment, the extraction member 46 may be an extraction net 152, as shown in FIG. 10. The medical instrument 32 may otherwise be the same as, or similar to, that shown in FIG. 3. According to this alternative embodiment, the method 800 may further include a step of deploying the extraction net 152 after positioning the extraction net 152 on the distal side of the material 10.

In yet another alternative embodiment, the dilation balloon may be formed of a sponge material, i.e., may be a dilation sponge. In this alternative embodiment, the dilation sponge may be contained within the sheath 40 until the medical instrument 32 is positioned within the bile duct 12. Then, the dilation sponge may be deployed, i.e., extended outside of the sheath 40, and may expand and dilate the bile duct 12. The dilation sponge may function in the same manner as that of the dilation balloon 44 described above, in that, during extraction of the material 10 from the bile duct 12, the dilation sponge dilates the bile duct 12 and the ampulla of Vater 22.

In addition, in another alternative embodiment, a dilation balloon 154 may be provided with a recess 156 in a distal facing surface 158 of the dilation balloon 154, as shown in FIGS. 11A-11C. The recess 156 may extend proximally from the distal facing surface 158, within a distal portion 160 of the dilation balloon 154, to a depth $D156$ that is less than or equal to a length of the distal portion 160. More specifically, the recess may have a depth $D156$ that is less than or equal to one-half of the length of the distal portion 160. In this alternative embodiment, the extraction member 46 is a balloon, and is positioned distal to the material 10 and inflated within the bile duct 12, and the dilation balloon 154 is positioned proximal to the material 10 and inflated, as shown in FIG. 11A. When the extraction member 46 is pulled proximally in step 810, the dilation balloon 154 remains stationary, and the extraction member 46 moves the material 10 in the bile duct 12 into the recess 156 of the inflated dilation balloon 154, as shown in FIG. 11B. Then, in a subsequent step, the extraction member 46 and the dilation balloon 154 may be deflated, as shown in FIG. 11C, thereby trapping or enclosing the material 10 within the recess 156. The treatment portion 38 may then be withdrawn from the bile duct 12, to safely and securely remove the material 10 from the bile duct 12.

In a modification of the embodiment described with respect to FIGS. 11A-11C, the dilation balloon 154 may have a fluid injection channel, in addition to the recess 156. The fluid injection channel may be connected to a fluid injection lumen of the tube 50. In this alternative embodiment, the method 800 may include a step of breaking up the material 10, after positioning the extraction member 46 distal of the material 10, and before the step 810 of pulling the extraction member 46 proximally. The step of breaking up the material 10 includes, for example, supplying fluid (e.g., water) at a high pressure to the fluid injection channel. As the water exits the water injection channel, the water is directed at the material, and breaks up the material 10 into pieces having relatively smaller sizes. The expanded extraction member 46 prevents small fragments of the material 10 from moving distally within the bile duct. Then, the extraction member 46 may be pulled proximally in step 810, thereby moving the pieces of the material 10 into the recess 156 of the dilation balloon 154. In a subsequent step, the extraction member 46 and the dilation balloon 154 may be deflated, thereby trapping the material 10 within the recess 156. The treatment portion 38 may then be withdrawn from the bile duct 12, to safely and securely remove the material 10 from the bile duct 12.

Although the medical instrument 32 is described as being used during an endoscopic procedure, the medical instrument 32 may be used in other medical procedures, such as a procedure to remove a kidney stone, for example.

By virtue of the medical instrument 32 of this disclosure, a material 10 can be safely and securely removed from a bile duct 12 of a subject, while preventing trauma to walls of the bile duct 12. The extraction member 46 and the dilation balloon 44 serve to trap the material 10 therebetween, preventing scraping or tearing of the walls of the bile duct 12 by the material 10.

The dilation balloon 44 of the embodiment shown in FIGS. 5A-5C provides for widening of the bile duct 12 directly proximal to the material 10, which reduces the potential trauma to the bile duct 12 caused by the material 10, and improves the maneuverability of the medical instrument 32. In addition, the tapered proximal portion 78 of the dilation balloon 44 allows for gradual dilation of the ampulla of Vater 22 at the entrance into the duodenum 18 (i.e., the opening between the bile duct 12 and the duodenum 18). Further, as noted above, the middle portion 80 of the dilation balloon 44 serves as an "anchor" that reduces the potential for the dilation balloon to slip into or out of the ampulla of Vater 22 during the endoscopic procedure.

The dilation balloon 114 of the embodiment shown in FIGS. 6A-6C similarly provides for widening of the bile duct 12 directly proximal to the material, which reduces the potential trauma to the bile duct 12 caused by the material 10, and improves the maneuverability of the medical instrument 32. The shape of the distal facing surface 130, including the concavity thereof, provides for relatively more secure entrapment of the material 10 during the procedure. Similarly to the tapered proximal portion 78 of the dilation balloon 44, the tapered proximal portion 118 of the dilation balloon 114 allows for gradual dilation of the ampulla of Vater 22 at the entrance into the duodenum 18. In addition, similarly to the middle portion 80 of the dilation balloon 44, the middle portion 120 of the dilation balloon 114 serves as an "anchor" that reduces the potential for the dilation balloon to slip into or out of the ampulla of Vater 22 during the endoscopic procedure.

In addition, the dilation balloon 132 of the embodiment shown in FIGS. 7A-7C similarly provides for widening of the bile duct 12 directly proximal to the material 10, reducing the potential trauma to the bile duct caused by the material 10, and improving the maneuverability of the medical instrument 32. Similarly to the tapered proximal portion 78 of the dilation balloon 44, the tapered proximal portion 136 of the dilation balloon 132 allows for gradual dilation of the ampulla of Vater 22 at the entrance into the duodenum. In addition, similarly to the middle portion 80 of the dilation balloon 44, the middle portion 140 of the dilation balloon 132 serves as an "anchor" that reduces the potential for the dilation balloon to slip into or out of the ampulla of Vater 22 during the endoscopic procedure. The dilation balloon 132 of this embodiment, and, in particular, the proximal biconvex portion 138 of the dilation balloon 132, accounts for variations in anatomy that may require a relatively larger portion of the dilation balloon 132 on a proximal end of the treatment portion 38, closest to the duodenum 18, during the endoscopic procedure.

In addition, by virtue of positioning and inflating the dilation balloon 44 of the medical instrument 32, as described herein, a lumen on a proximal side of a material 10 can be increased or dilated in a controlled manner, thereby reducing a force needed to pull the material 10 out of the bile duct 12, and, in turn, reducing a risk of the extraction member 46 bursting, in the case in which the extraction member 46 is a balloon. The hourglass shape of the dilation balloon 44 provides for smooth stretching of the bile duct 12 and/or the ampulla of Vater 22 during the endoscopic procedure, and, in particular, during withdrawal of the material 10. In addition, in a case in which the bile duct 12 of the subject is a "sigmoid" bile duct, e.g. curved or crescent-shaped, the dilation balloon 44 dilates the bile duct 12, reducing the need for torqueing by an operator performing the procedure.

Also, by virtue of the medical instrument 32 and the related method 800 described herein, a single device is provided for use during an endoscopic procedure, such as an EPBD. As a result, the problems associated with using multiple devices, including tangling of the devices during insertion or exchanging thereof, loss of positioning of the guidewire, increased costs associated with the procedure, increased time needed to complete the procedure, increased invasiveness and aggravation of the gastrointestinal tract of the subject, and increased risk to the subject for infection or injury, can be eliminated and/or reduced.

While principles of the disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:
1. A medical instrument comprising:
a tube;
a sheath provided around the tube and coaxial with the tube;
an inflatable balloon provided at a distal end of the sheath, the balloon being configured to receive a fluid from a lumen of the sheath, and the balloon having:
  a central opening along a longitudinal axis thereof, and into which the tube extends;
  a proximal portion;
  a middle portion adjacent to and distal of the proximal portion; and
  a distal portion adjacent to and distal of the middle portion, the distal portion including a planar distal-facing surface and a distal neck distal of and perpendicular to the distal-facing surface,
  wherein, in response to inflation, a maximum diameter of the middle portion is less than or equal to a maximum diameter of the proximal portion, and is less than a maximum diameter of the distal portion; and
an extraction member provided at a distal end of the tube, distal to the balloon, and movable axially relative to the balloon.

2. The medical instrument of claim 1, wherein a distal end of the sheath is positioned within the central opening of the balloon.

3. The medical instrument of claim 1, wherein the extraction member has a central opening along a longitudinal axis thereof, into which the tube extends.

4. The medical instrument of claim 1, wherein the extraction member is one of:
a balloon, configured to receive a fluid from a lumen of the tube; and
a net.

5. The medical instrument of claim 1, wherein the proximal portion of the balloon includes a proximal tapered portion.

6. The medical instrument of claim 1, wherein the proximal portion of the balloon includes a spherical distal portion and a proximal tapered portion.

7. The medical instrument of claim 1, wherein the distal portion of the balloon is cylindrical with respect to a longitudinal axis thereof.

8. The medical instrument of claim 1, wherein the distal portion of the balloon has a portion having a shape of at least part of a sphere.

9. The medical instrument of claim 1, wherein the maximum diameter of the proximal portion is equal to the maximum diameter of the middle portion of the balloon.

10. The medical instrument of claim 1, wherein the maximum outer diameter of the proximal portion is less than the maximum outer diameter of the distal portion of the balloon.

11. The medical instrument of claim 1, wherein a length of the proximal portion of the balloon is greater than each of a length of the distal portion and a length of the middle portion of the balloon, with respect to a longitudinal axis of the balloon, and the length of the middle portion is less than or equal to the length of the distal portion.

12. The medical instrument of claim 1, wherein the tube includes a distal opening, and a lumen of the tube is configured to receive a guidewire that can extend past the distal opening of the tube.

13. The medical instrument of claim 1, wherein the middle portion defines a curved biconcave profile.

14. The medical instrument of claim 13, wherein a maximum diameter of the proximal portion is greater than a maximum diameter of the distal portion, wherein the maximum diameter of the distal portion is greater than a minimum diameter of the middle portion.

15. The medical instrument of claim 13, wherein a maximum diameter of the distal portion is greater than a maximum diameter of the proximal portion, wherein the maximum diameter of the proximal portion is greater than a minimum diameter of the middle portion.

16. A medical instrument comprising:

a tube;

a sheath provided around the tube and coaxial with the tube;

a balloon provided at a distal end of the sheath and having a longitudinal axis extending therethrough, the balloon being configured to be inflated via a lumen of the sheath, the balloon including a distal-facing concave surface and a distal neck extending distally from a radially inward edge of the distal-facing concave surface, wherein the distal neck extends proximally of a plane perpendicular to the longitudinal axis and positioned at a most distal point of the distal-facing concave surface, wherein, in response to inflation, the balloon has an hourglass shape; and an extraction member provided at the distal end of the tube, distal to the balloon.

17. The medical instrument of claim 16, wherein the hourglass shape is defined by a proximal bulb portion, a middle neck portion, and a distal bulb portion.

18. The medical instrument of claim 17, wherein the distal surface of the distal bulb portion of the balloon defines a recess extending radially inward and proximally toward the proximal bulb portion of the balloon, the recess being configured to house a biliary stone.

19. A method of removing material from a subject, the method comprising:

advancing a device into a lumen of the subject, the device including:
  a tube;
  a sheath provided around the tube and coaxial with the tube;
  a dilation balloon provided at a distal end of the device, the dilation balloon having:
    a central opening along a longitudinal axis thereof, the central opening receiving the tube;
    a proximal portion;
    a middle portion adjacent to and distal of the proximal portion; and
    a distal portion adjacent to and distal of the middle portion, the distal portion having a distal-facing concave surface; and
  an extraction member provided at a distal end of the tube, and distal of the dilation balloon;

positioning the extraction member distally of the material;

positioning the dilation balloon proximally of the material;

inflating the dilation balloon so that a maximum diameter of the middle portion of the dilation balloon is less than or equal to a maximum diameter of the proximal portion of the dilation balloon, and less than a maximum diameter of the distal portion of the balloon pulling at least the extraction member proximally to pull the material proximally; and capturing the material within the distal-facing concave surface while the dilation balloon is inflated.

20. The method of claim 19, wherein the extraction member includes an extraction balloon, and the method further comprises inflating the extraction balloon before or after the inflating of the dilation balloon wherein the dilation balloon includes a first marker band positioned between the distal portion and the middle portion and a second marker band positioned between the proximal portion and the middle portion, and the method further comprising: using the first marker band and the second marker band to confirm that the distal portion is positioned within a bile duct.

* * * * *